United States Patent
Long et al.

(10) Patent No.: US 9,540,294 B2
(45) Date of Patent: Jan. 10, 2017

(54) METAL-ORGANIC FRAMEWORK FOR THE SEPARATION OF ALKANE ISOMERS

(71) Applicant: THE REGENTS OF THE UNIVERSITY OF CALIFORNIA, Oakland, CA (US)

(72) Inventors: Jeffrey R. Long, Oakland, CA (US); Zoey R. Herm, Berkeley, CA (US); Brian M. Wiers, Berkeley, CA (US); Rajamani Krishna, Amsterdam (NL)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 70 days.

(21) Appl. No.: 14/703,631

(22) Filed: May 4, 2015

(65) Prior Publication Data

US 2015/0307419 A1    Oct. 29, 2015

Related U.S. Application Data

(63) Continuation of application No. PCT/US2013/068416, filed on Nov. 5, 2013.

(60) Provisional application No. 61/722,667, filed on Nov. 5, 2012.

(51) Int. Cl.
| | |
|---|---|
| C07C 7/12 | (2006.01) |
| C07F 15/02 | (2006.01) |
| C07B 63/00 | (2006.01) |
| B01J 20/22 | (2006.01) |
| C07C 5/27 | (2006.01) |
| C10G 25/00 | (2006.01) |

(52) U.S. Cl.
CPC ............... *C07C 7/12* (2013.01); *B01J 20/226* (2013.01); *C07B 63/00* (2013.01); *C07C 5/277* (2013.01); *C07C 5/2732* (2013.01); *C07F 15/02* (2013.01); *C10G 25/003* (2013.01); *C10G 2400/02* (2013.01)

(58) Field of Classification Search
CPC .................................. C07C 7/12; C07F 15/02
See application file for complete search history.

(56) References Cited

FOREIGN PATENT DOCUMENTS

| WO | 2006089908 A1 | 8/2006 |
| WO | 2010133891 A1 | 11/2010 |
| WO | 2012122233 A2 | 9/2012 |

OTHER PUBLICATIONS

Bloch et al. "Hydrocarbon Separations in a Metal-Organic Framework with Open Iron(II) Coordination Sites" Science, 2012, vol. 335, pp. 1606-1610.*
Korean Intellectual Property Office (KIPO), International Search Report and Written Opinion, PCT International Application No. PCT/US2013/068416, issued Feb. 12, 2014, pp. 1-6, with claims searched, pp. 7-10, counterpart to U.S. Appl. No. 14/703,631.
Herm, Z. R., et al., "Separation of hexane isomers in a metal-organic framework with triangular channels", Science, May 24, 2013, vol. 340, pp. 960-964.
Bloch, E.D. et al., "Hydrocarbon separations in a metal-organic framework with open Iron (II) coordination sites", Science, Mar. 30, 2012, vol. 335, pp. 1606-1610.

* cited by examiner

*Primary Examiner* — Joseph Kosack
(74) *Attorney, Agent, or Firm* — O'Banion & Ritchey LLP; John P. O'Banion

(57) ABSTRACT

A metal organic framework $Fe_2(bdp)_3$ ($BDP^{2-}$=1,4-benzene-dipyrazolate) with triangular channels is particularly suited for C5-C7 separations of alkanes according to the number of branches in the molecule rather than by carbon number. The metal-organic framework can offer pore geometries that is unavailable in zeolites or other porous media, facilitating distinct types of shape-based molecular separations.

19 Claims, 8 Drawing Sheets

METAL-ORGANIC FRAMEWORK FOR THE SEPARATION OF ALKANE ISOMERS

CROSS-REFERENCE TO RELATED APPLICATIONS

This application is a 35 U.S.C. §111(a) continuation of PCT international application number PCT/US2013/068416 filed on Nov. 5, 2013, incorporated herein by reference in its entirety, which claims priority to, and the benefit of, U.S. provisional patent application Ser. No. 61/722,667 filed on Nov. 5, 2012, incorporated herein by reference in its entirety. Priority is claimed to each of the foregoing applications.

The above-referenced PCT international application was published as PCT International Publication No. WO 2014/071351 on May 8, 2014, which publication is incorporated herein by reference in its entirety.

STATEMENT REGARDING FEDERALLY SPONSORED RESEARCH OR DEVELOPMENT

This invention was made with Government support under DE-SC0001015 awarded by the Department of Energy (DOE). The Government has certain rights in the invention.

INCORPORATION-BY-REFERENCE OF MATERIAL SUBMITTED IN A COMPUTER PROGRAM APPENDIX

Not Applicable

BACKGROUND OF THE INVENTION

1. Field of the Invention

This invention pertains generally to fluid stream separation schemes and methods for producing metal-organic frameworks, and more particularly to the production and use of a metal-organic framework with the formula $Fe_2(BDP)_3$ which can efficiently separate the isomers of C5-C7 alkanes.

2. Description of Related Art

The separation of molecules that are structurally-similar and chemically-similar from a product stream can be particularly challenging. Conventional separation schemes use solid adsorbents such as zeolites and activated carbons for key gas storage and molecular separation applications. However, these separations are often dependent on cryogenic or distillation steps that are both extremely energy-intensive strategies and often inefficient resulting in the production of low purity separations. For example, the efficient separation of alkane isomers by adsorption is especially challenging because the molecules are chemically inert and have similar polarizabilities, leaving shape as the main handle available for their differentiation. This alkane separation is critical to the production of gasoline, which is composed of approximately ten percent pentanes and hexanes.

For example, high-octane gasolines are more expensive than regular gasolines because of the cost and difficulty of separating the right type of molecules from crude petroleum. The creation of premium fuels requires the refinery to boil the petroleum at precise temperatures to separate out alkane isomers with only slightly different boiling points making the overall process both challenging and costly.

Hexanes of formula $C_6H_{14}$ are generated in large quantities through a catalytic isomerization reaction that results in a thermodynamically-controlled product stream composed of 10% to 30% of each of five different isomers. The product stream from the isomerization reactor, that commonly uses the zeolite MOR as a catalyst, consists of an equilibrium distribution of unreacted n-hexane (nC6), along with its mono-branched isomers 2-methylpentane (2MP), 3-methylpentane (3MP) and di-branched isomers 2,2-dimethylbutane (22DMB) and 2,3-dimethylbutane (23DMB).

In current industrial practice, the linear nC6 is separated from the branched isomers in an adsorption separation step that relies on molecular sieving. The typical adsorbent that is used is LTA-5A that consists of cages separated by 4.1 Å sized windows. The windows only allow the diffusion and adsorption of the linear nC6 isomer, and the branched isomers are rejected and removed as product. The unreacted nC6 is then recycled back to the isomerization reactor.

The worth of a particular isomer as a component in the gasoline pool is related to its research octane number (RON), which is highest for the di-branched hexanes 2,3-dimethylbutane and 2,2-dimethylbutane, that have values of 105 and 94, respectively. The RON values for the mono-branched isomers 2-methylpentane and 3-methylpentane are significantly lower, at 74 and 75, respectively, whereas the value for linear n-hexane is only 30. To achieve higher octane number fuel blends, current processes sieve n-hexane using zeolites, generating a mixture of the other four isomers with a final RON value of nearly 83, while returning n-hexane to the isomerization reactor. Additionally, some separation processes achieve higher-grade mixtures by subsequently distilling the mono-branched isomers away from the valuable dimethylbutane products. At the present time, approximately two million barrels of pentanes and hexanes are processed daily.

Therefore, di-branched isomers are preferred products for incorporation into the high-octane gasoline pool. An improved process would require the recycle of both linear and mono-branched isomers to the reactor. Typically, in such a processing scheme the aim would be to produce a product stream from the separation step with a RON value of 92. The separation of 22DMB and 23DMB from the remaining isomers is a difficult task because it requires distinguishing molecules on the degree of branching.

Accordingly, there is an need for an improved hexane separation process that selectively isolates the most valuable products, 2,3-dimethylbutane and 2,2-dimethylbutane, while returning the less valuable mono-branched isomers to the isomerization reactor along with n-hexane.

There is also a need for a system that performs this separation at or near the isomerization temperature thereby saving a great deal of energy in the production of high-quality gasoline. Furthermore, such a scheme would potentially benefit public health, since it could reduce the need to use toxic aromatics that are added to boost the octane number of gasoline.

The present invention satisfies these needs as well as others and is generally an improvement over the art.

BRIEF SUMMARY OF THE INVENTION

Metal-organic frameworks can offer pore geometries that are unavailable in zeolites or other porous media, facilitating distinct types of shape-based molecular separations. The efficient separation of alkane isomers by adsorption is especially challenging, because the molecules are chemically inert and have similar polarizabilities, leaving shape as the main characteristic that is available for their differentiation. This particular separation is critical to the production of gasoline, which is composed of approximately ten percent pentanes and hexanes.

The present invention is directed to a metal-organic framework featuring sharply-angled pore walls of a type not encountered in zeolites, and capable of fractionating alkane isomers according to the degree of branching. By way of example, and not of limitation, the invention can be illustrated by a metal-organic framework with the formula $Fe_2(BDP)_3$ ($BDP^{2-}$=1,4-benzenedipyrazolate), a highly-stable framework with triangular channels. The functionality of the framework was illustrated by the separation of isomers of C5-C7 alkanes according to the degree of branching. This separation was demonstrated via equilibrium adsorption of pure 2,2-dimethylbuane (22DMB), 2,3-dimethylbutane (23DMB), 3-methylpentane (3MP), 2-methylpentane (2MP), and n-hexane (nC6) as well as experimental and theoretical dynamic adsorption of a mixture of these vapors.

Consistent with the varying abilities of the isomers to wedge along the triangular corners of the $Fe_2(BDP)_3$ structure, adsorption isotherms and calculated isosteric heats indicated an adsorption selectivity order of n-hexane>2-methylpentane>3-methylpentane>2,3-dimethylbutane≈2,2-dimethylbutane. A breakthrough experiment performed at 160° C. with an equimolar mixture of all five molecules confirmed that the di-branched isomers eluted first from a bed packed with $Fe_2(BDP)_3$, followed by the mono-branched isomers, and finally linear n-hexane. Configurational bias Monte Carlo simulations also confirmed the functionality of the molecular separation.

In this context, the present invention provides an improved hexane separation process that selectively isolates the most valuable products, 2,3-dimethylbutane and 2,2-dimethylbutane, while returning the less valuable mono-branched isomers to the isomerization reactor along with n-hexane for further processing. Thermodynamic separation of hexane (or pentane) isomers has been shown in porous materials, however, never at industrially-relevant temperatures or pressures or with the crucial separation of 2,2-dimethylbutane and 2,3-dimethylbutane from linear hexane and the two methylpentanes. Performing this separation at or near the isomerization temperature can save a great deal of energy in the production of high-quality gasoline. Further, the process may benefit public health, since it can reduce the usage of toxic aromatic additives, which are currently added to boost the octane number of gasoline.

According to one aspect of the invention, a method for separating alkane isomers by shape characteristics at industrial temperatures and pressures is provided. This method can be used in refineries as part of the isomerization process, which currently only separates out n-hexane and leaves the less-valuable methylpentane isomers mixed with the dimethylbutane isomers.

Another aspect of the invention is to provide a system for separating mixtures of isomers and other structurally and chemically similar molecules that is efficient and avoids the need for distillation or exposure to extreme temperatures for separation.

According to another aspect of the invention, a metal-organic framework with the formula $Fe_2(BDP)_3$ is provided which can efficiently separate the isomers of C5-C7 alkanes. Further, this material could replace the currently-used zeolite 5A and improve the separation of n-hexane from the other four hexane isomers.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes several embodiments of the system scheme of the present invention are depicted generally in FIG. 1A through FIG. 8 and the associated methods for producing the metal-organic framework or separator apparatus. It will be appreciated that the methods may vary as to the specific steps and sequence and the apparatus architecture may vary as to structural details, without departing from the basic concepts as disclosed herein. The method steps are merely exemplary of the order that these steps may occur. The steps may occur in any order that is desired, such that it still performs the goals of the claimed invention.

Figure 1A:
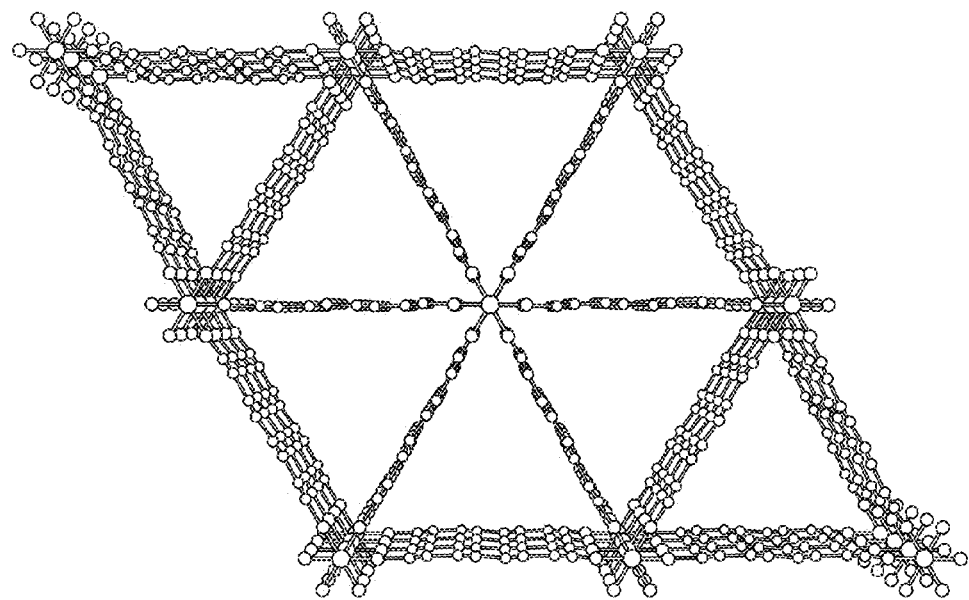
FIG. 1A is a representation of the metal-organic framework $Fe_2(BDP)_3$ with the view taken along the [001] direction in the orthorhombic crystal structure (space group Fddd) and the H atoms omitted for clarity.
Figure 1B:
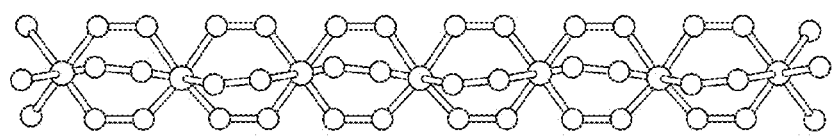
FIG. 1B is a perpendicular view of the one-dimensional chains of pyrazolate-bridged $Fe^{III}$ octahedra.

Turning now to FIG. 1A, FIG. 1B and Example 1, a metal-organic framework with the formula $Fe_2(BDP)_3$ is provided that is particularly suited for the separation of the isomers of C5-C7 alkanes. As described in Example 1, the solvothermal reaction of $H_2BDP$ ($BDP^{2-}$=1,4-benzenedipyrazolate) and Fe(acetylacetonate)$_3$ in dimethylformamide at 393 K for 24 hours produces the $Fe_2(BDP)_3$ framework. Heating the as-synthesized $Fe_2(BDP)_3$ to 453 K under an 8 microTorr vacuum for 24 hours produced a porous solid with a Brunauner-Emmett-Teller surface area of 1230 $m^2/g$.

The view in FIG. 1 is along the [001] direction in the orthorhombic crystal structure (space group Fddd) and illustrates the triangular channel structure of the material. The synthesized product is a porous solid with one-dimensional, equilateral triangular shaped channels as seen in FIG. 1A.

Throughout the structure run chains of octahedrally-coordinated $Fe^{III}$ atoms bridged by the N—N pyrazolate bonds. The centroid-to-centroid Fe—Fe distance along the edge of the pore is 13.26 Å. FIG. 1B depicts a perpendicular view of the one-dimensional chains of pyrazolate-bridged $Fe^{III}$ octahedra. Selected interatomic distances (Å) and angles (deg): Fe—N1x 1.981(2), Fe—N2 2.04(1), Fe—N1 1.94(1); Fe . . . Fe (vertex to vertex) 13.255(1), Fe—Fe (nearest neighbor) 3.852(4); N1x-Fe-N2 96.698(1), N1x-Fe-N2' 92.479(1), N1x-Fe-N1 81.236(1), N1x-Fe-N1' 88.946(1), N1-Fe-N2 91.65(2); Fe—N1x-N1x 123.070(1), Fe—N2-N1 115.592(1), Fe—N1-N2 130.994(1).

The size and shape of the triangular channels of $Fe_2(BDP)_3$ have direct implications on the capability of the framework for the separation of alkane isomers. The channel dimensions are big enough to accommodate all five hexane isomers, and therefore the separation will not be the result of sieving, and the acute angles of the pore allow for enhanced van der Waals interactions with the guest alkanes/paraffins.

Generally, the backbone of the alkane molecule becomes aligned along the triangular gutters (vertices) within the channels, which provides the maximum surface area for interactions. The number of carbon atoms in the backbone that can exert van der Waals interactions with the framework atoms in the vertices is of vital importance. From the observed conformations, it is evident that the number of carbon atoms that can effectively interact with the pore wall decreases with the degree of branching. The di-branched isomers are more compact and have the least amount of van der Waals interactions with the walls.

One prominent distinction between the structure of conventional zeolites and metal-organic frameworks is in the angles that are present in the internal pore walls. The pore contours defined by a zeolite scaffolding are necessarily obtuse as a result of the O—Si—O and Si—O—Si angles of ~109° and >130°, respectively. In contrast, the higher coordination numbers possible for the metal nodes within a metal-organic framework can give rise to flat pore surfaces that intersect at acute angles. This can be seen in the structure of the metal-organic framework $Fe_2(BDP)_3$ shown in FIG. 1A. In this structure, octahedral iron(III) centers are linked via $\mu^2$-pyrazolate units to form chains running along one crystal axis, where both nitrogens on one ring bind to different iron atoms. The rigid, nearly planar $BDP^{2-}$ ligands define a corrugated triangular channel structure featuring sharply-angled crevices running along the triangle corners. The chains of octahedral iron(III) centers form the vertices of these triangles. The corrugated structure of the channels with regular crevices may provide strong van der Waals contacts for linear alkanes, whereas branched alkanes would be more likely to wedge themselves within the corners.

The framework of $Fe_2(BDP)_3$ is analogous to the carboxylate-linked structure of $Sc_2(BDC)_3$ ($BDC^{2-}$=1,4-benzenedicarboxylate), but with a larger metal to metal atom triangle edge length of 13.25(2) Å as a result of the longer $BDP^{2-}$ linker. The structure is also related to that of Co(BDP), wherein chains of tetrahedral cobalt(II) centers lead instead to square channels.

The strong iron(III)-pyrazolate bonds and highly-connected architecture of $Fe_2(BDP)_3$ provide the material with exceptional chemical and thermal stability. The material can be boiled in aqueous solutions at pH 2-10 for two weeks, or heated in air to at least 280° C., without losing crystallinity.

Configurational bias Monte Carlo simulations illustrate why the pores or channels are ideal for separating dimethylbutanes from methylpentanes and linear hexane. The CBMC calculations suggest that the size of the channels in $Fe_2(BDP)_3$ are nearly optimal for a hexane isomer separation. Narrower triangular channels cannot accommodate all five isomers, while wider channels do not maximize the differences in van der Waals contacts.

CBMC simulations also confirm that $Fe_2(BDP)_3$ is similarly suitable for separating pentane and heptane isomers according to the degree of branching. For pentane isomers, the results indicate the hierarchy of adsorption strengths as n-pentane>2-methylbutane>neopentane. By comparison, heptanes follow the order n-heptane>2-methylhexane≈3-methylhexane>2,2-dimethylpentane 2,3-dimethylpentane. Accordingly, pulse chromatographic separations and simulations revealed the extraordinary ability of $Fe_2(BDP)_3$ to separate the di-branched alkanes with high RON values from a mixture of pentane, hexane, and heptane isomers.

Figure 2:
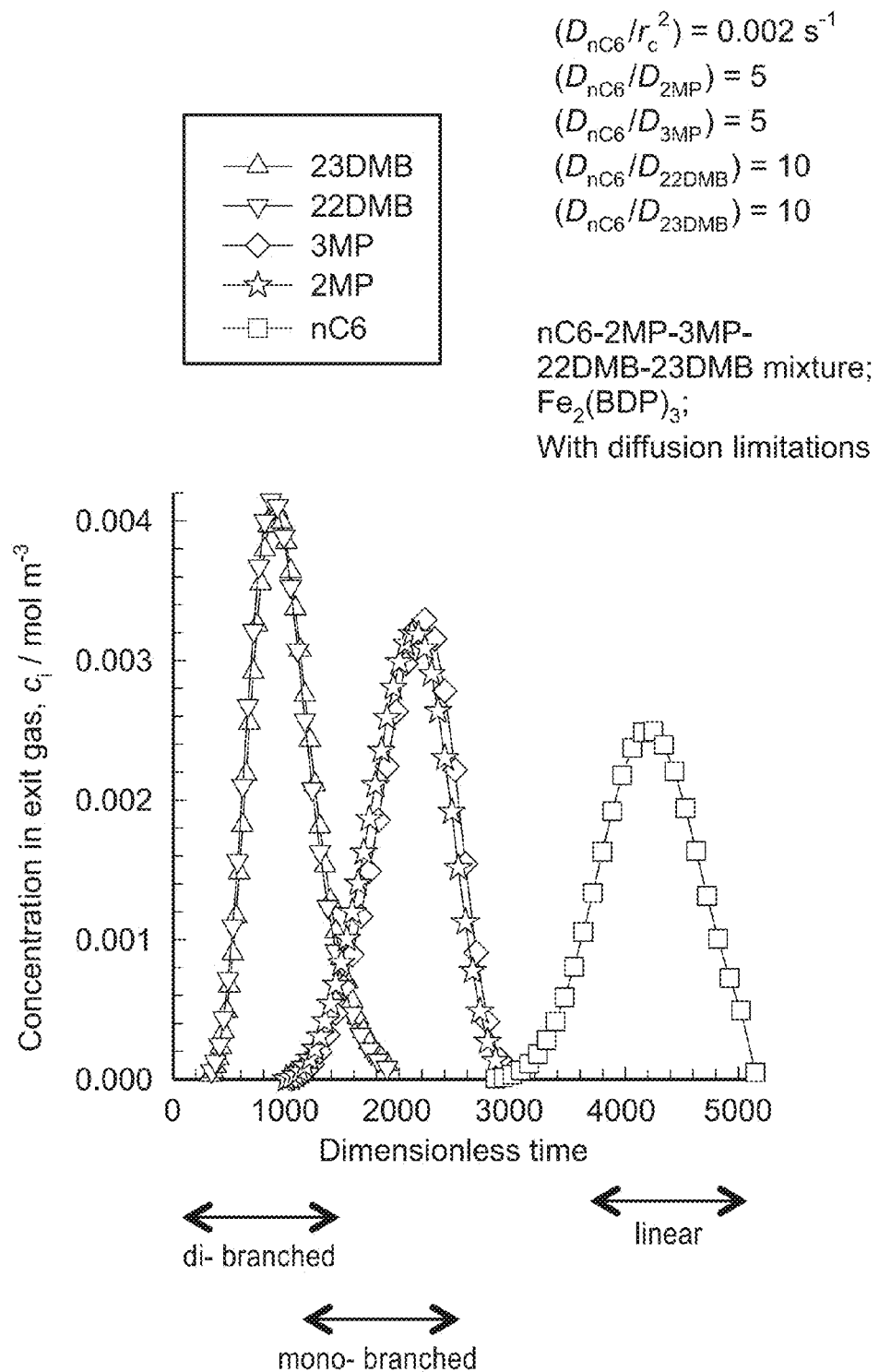
FIG. 2 is a pulse chromatograph of separations for the hexane mixture (nC6-2MP-3MP-22DMB-23DMB) by $Fe_2(BDP)_3$ from experimental isotherms.

Turning now to FIG. 2, a pulsed chromatogram based on experimental isotherms for hexanes is shown. The shape of the isotherms of the five hexane isomers adsorbing onto $Fe_2(BDP)_3$ is relevant to their ability to be separated. Pulse chromatographic simulations for separations ranging from 3-component pentanes such as nC5/2 MB/neoP to 13-component combinations of pentanes, hexanes and heptanes using $Fe_2(BDP)_3$ were also conducted and evaluated. These separations demonstrated the adsorption selectivity and the ability of $Fe_2(BDP)_3$ to perform shape based molecular separations.

Breakthrough experiments with feeds of these multiple alkane components further illustrate the isomer separation ability of $Fe_2(BDP)_3$. When an equimolar mixture is directed through a bed of $Fe_2(BDP)_3$ material at 160 K, pure 2,2-dimethylbutane was shown to elute first. Then, the higher octane number 2,3-dimethylbutane breaks through the column. After these almost reach equilibrium, the methylpentanes elute together, followed later by n-hexane. The dimethylbutane isomer mixture is the most valuable fraction of the five isomers, and demonstrates the possibility of separating dimethylbutanes (22DMB-23DMB) from methylpentanes (2MP-3MP) and n-hexane (nC6).

Figure 3:
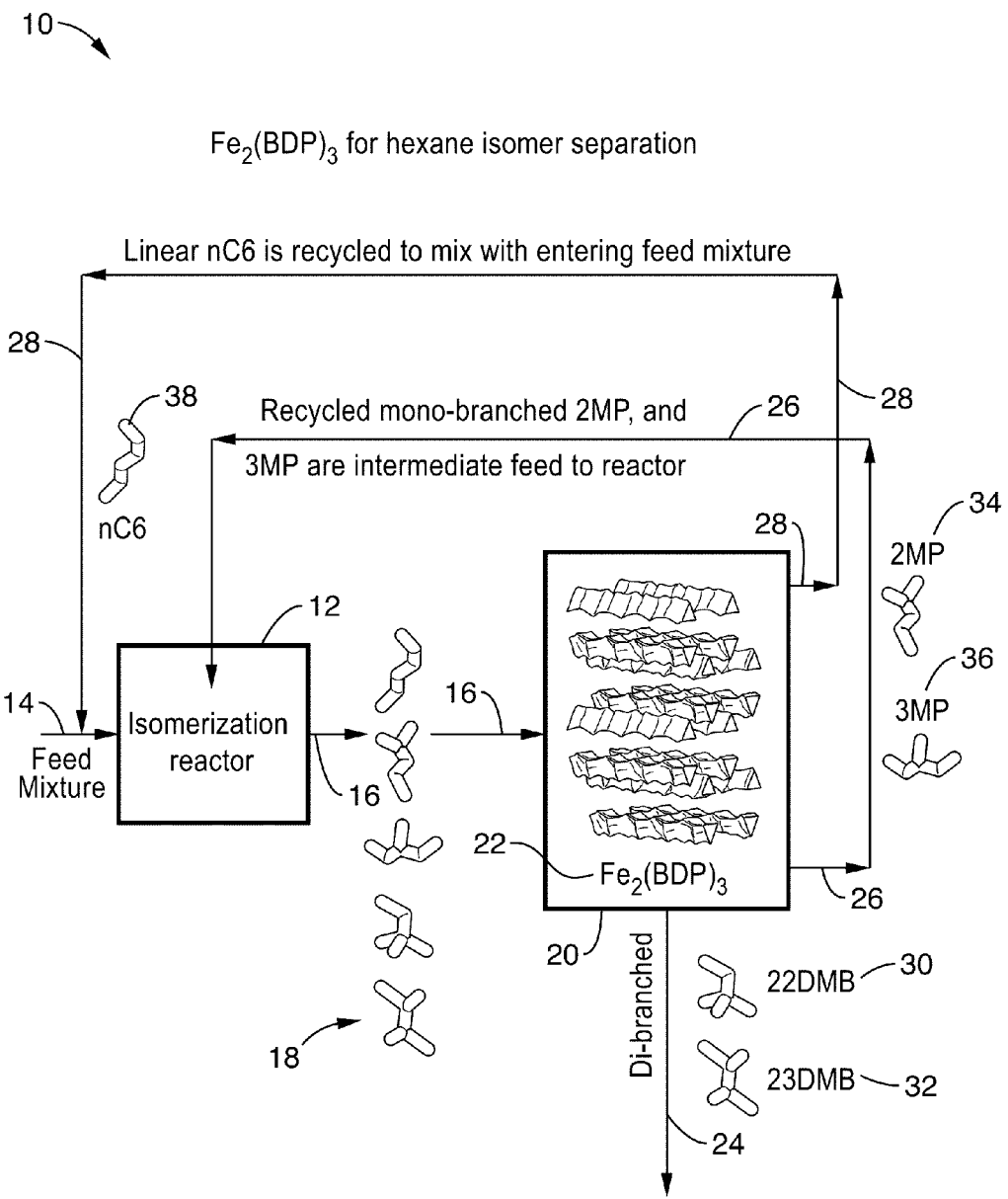
FIG. 3 is a schematic representation of one embodiment of an alkane isomerization process incorporating $Fe_2(BDP)_3$ in the separation step and with staged recycling of linear nC6 and mono-branched 2MP and 3MP to the isomerization reactor according to the invention.

The embodiment of the system 10 shown schematically in FIG. 3 is adapted for the separation of hexane isomers according to the degree of branching for fuel production that does not employ molecular sieving with zeolites or distillation. In this context, a conventional isomerization reactor 12 receives a feed of a mixture 14 of gases or liquids for isomerization in the reactor 12. The reactor 12 can be configured to produce many different products. Since the isomerization of straight chained alkanes is a slightly exothermic reaction, the yield of branched alkane isomers will be thermodynamically favored by low reaction temperatures in the reactor 12.

In the illustration of FIG. 3, the separation of hexane isomers takes place in reactor 12 to produce an output 16 of C6 fluid 18 generally comprising five alkanes: 23DMB, 22DMB, 3-MP, 2-MP and nC6. The output 16 of the isomerization reactor 12 is sent through a separator 20 that is filled with the $Fe_2(BDP)_3$ framework material 22. In this embodiment, the separator 20 has an outflow shown schematically as a di-branched output 24, a mono-branched output 26 and a linear chain output 28. However, the outflow from the separator can be through a single duct and downstream valves directing the material emerging from the separator to the desired location.

The di-branched output 24 collects the valuable branched butanes (22 DMB) 30 and (23 DMB) 32 that have been separated leaving the mono-branched pentanes (2MP) 34 and (3MP) 36 along with the linear hexane (nC6) 38 to be processed further.

The mono-branched output 26 of the separator 20 can be recycled and directed back to the isomerization reactor 12 or the output of 2MP and 3MP can be isolated and stored for further use in other settings. Likewise, the n-hexane 38 of separator output 28 can be recycled back to the initial feed mixture 14 and reintroduced back into the isomerization reactor 12. The composition of the feed mixture 14 and the concentration of mono-branched pentanes in the reactor 12 can be controlled with the selective recycling of separated mono-branched and linear alkanes in the system.

Accordingly, the $Fe_2(BDP)_3$ framework material separates hexane isomers at a representative temperature of an isomerization reactor (~433 K), therefore requiring no additional energy to heat or cool the input gas stream 16 entering the separator 20. This was established with equilibrium adsorption evaluations of each hexane isomer, the behavior of an equimolar mixture of the five hexane isomers directed through a bed of $Fe_2(BDP)_3$, neutron diffraction of n-hexane bound to $Fe_2(BDP)_3$, and configurational bias Monte Carlo simulations of pentane, hexane, and heptane isomer behavior.

Figure 4:
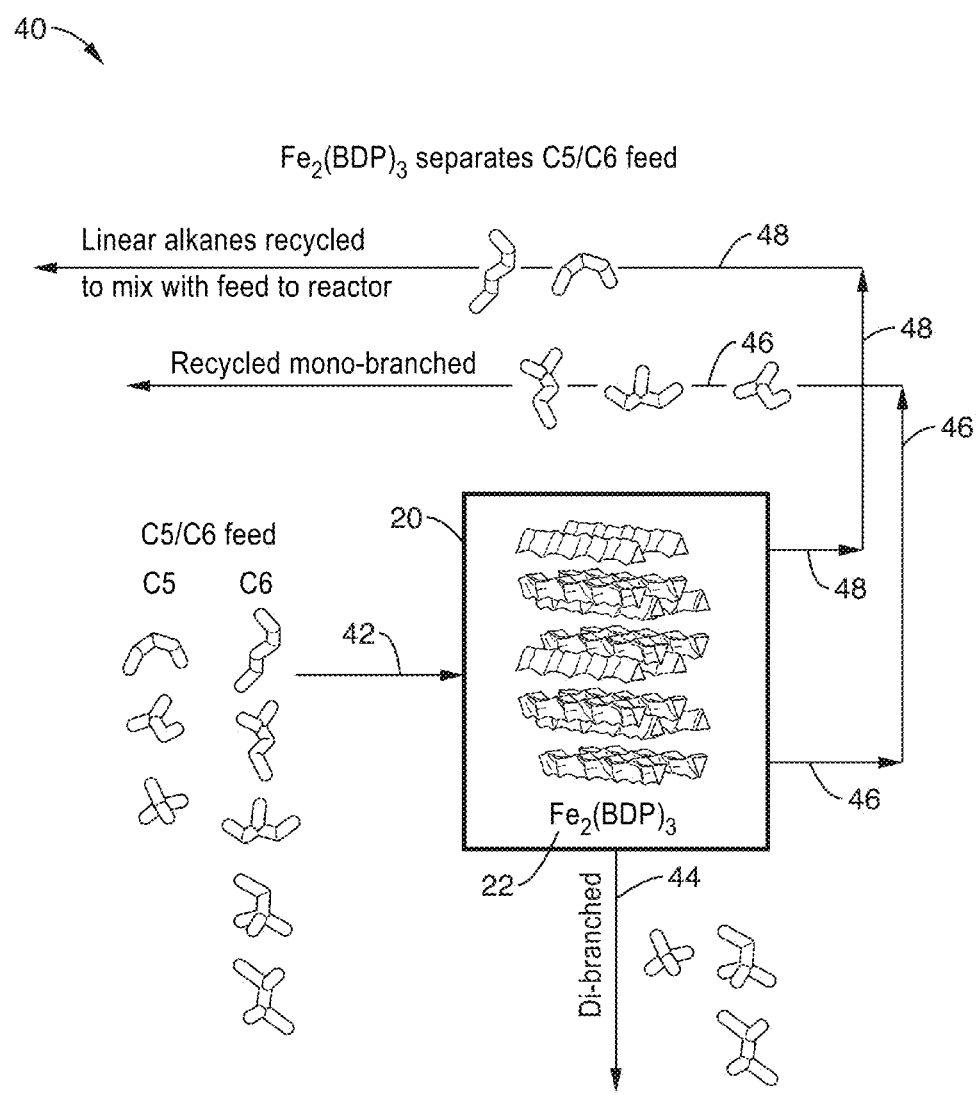
FIG. 4 is a schematic representation of one embodiment of an alkane isomerization process incorporating $Fe_2(BDP)_3$ in the separation step of a C5/C6 feed and with staged recycling of linear nC6 and mono-branched alkanes to an isomerization reactor according to the invention.

FIG. 4 is an alternative system embodiment 40 adapted for separating a C5/C6 mixed feedstock incorporating $Fe_2(BDP)_3$ in the separation step. The input feed 42 from the isomerization reactor or some other source to separator 20 provides the C5/C6 mixture 42 for separation.

There can be three C5 gases and five C6 gases in the C5/C6 mixture feed in this reactor/separator configuration. The three C5 alkanes, formula $C_5H_{12}$, are: (a) pentane, with five carbon atoms forming a straight chain; (b) 2-methylbutane, with one methyl branch on the second carbon of a four-carbon chain; and (c) 2,2-dimethylpropane, that has two methyl branches on the second carbon of a three carbon chain.

The branched components of the C5/C6 alkane feed 42 from the reactor or other source are separated with the $Fe_2(BDP)_3$ bed 22 of the separator 20. The 22DMB, 23DMB and 2,2-dimethylpropane di-branched alkanes 44 are separated out for further use. The branched isomers of C5 and C6 alkanes can be valuable additives to the gasoline pool because they have high octane numbers compared to the straight chain isomers.

The separated mono-branched isomers 46 of (2MP), (3MP) and 2-methylbutane are preferably recycled and returned back to the reactor for further processing or removed from the system. The output feed 48 of linear alkanes of pentane and hexane (nC6) are preferably returned to the input feed to the reactor for isomerization. The output of desirable branched isomers is greatly increased with recycling and control over the composition of reactants in the isomerization reactor in this system.

Figure 5:
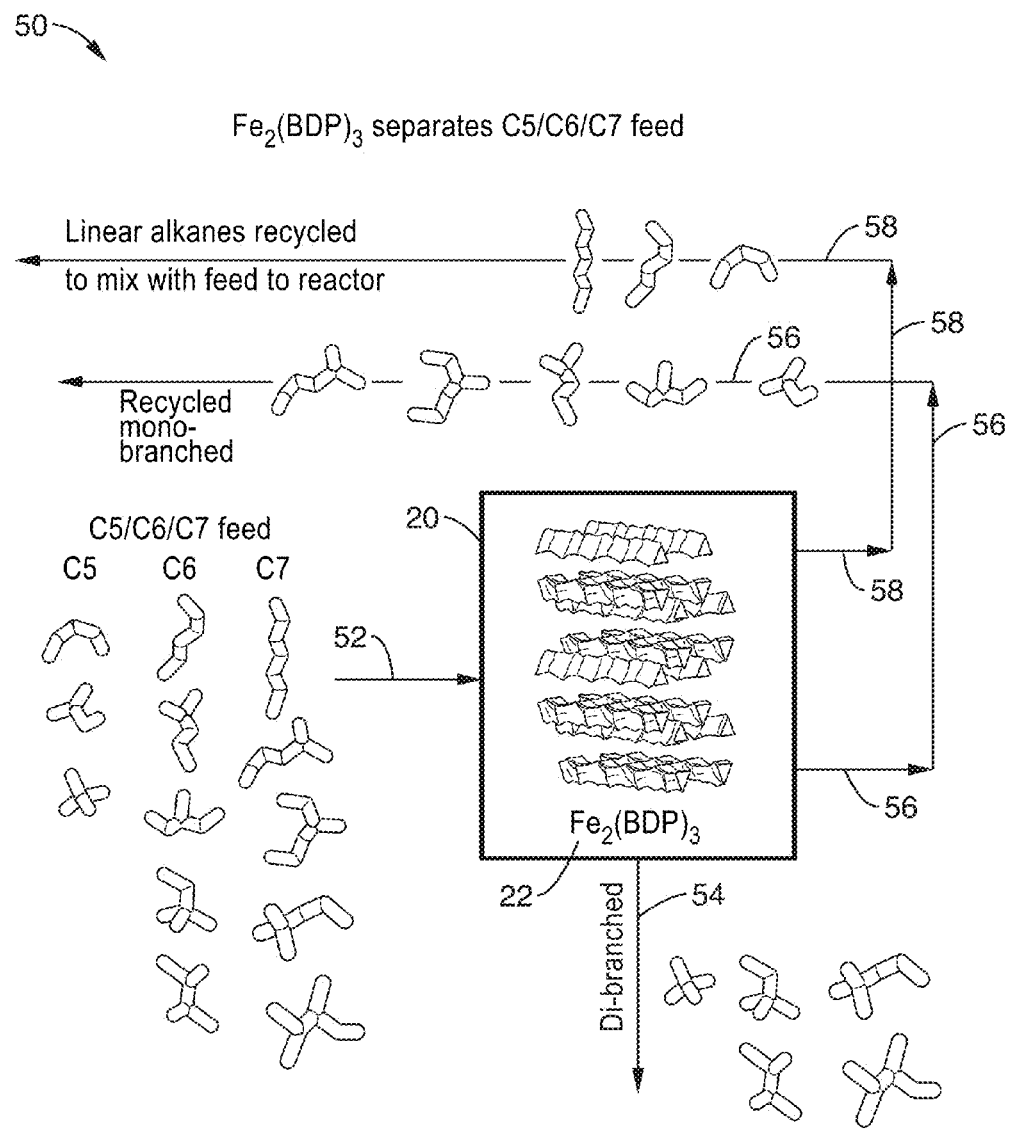
FIG. 5 is a schematic representation of one embodiment of an alkane isomerization process incorporating $Fe_2(BDP)_3$ in the separation step of a C5/C6/C7 feed and with staged recycling of linear nC6 and mono-branched alkanes to an isomerization reactor according to the invention.

Likewise, the separator 20 of $Fe_2(BDP)_3$ material 22 can be adapted for use with separations of other mixtures of alkanes. FIG. 5 is a schematic illustration of a C5/C6/C7 alkane isomerization process 50 incorporating $Fe_2(BDP)_3$ in the separation step and with staged recycling of linear nC6 and mono-branched isomers to the isomerization reactor. The input feed 52 of the C5/C6/C7 alkanes from a source to the separator 20 can include any mixture of pentanes, hexanes and heptanes from a source of alkanes like an isomerization reactor. There are nine structural isomers of heptane, formula $C_7H_{16}$, as follows: 1) heptanes; 2) 2-methylhexane; 3) 3-methylhexane; 4) 2,2-dimethylpentane; 5) 2,3-dimethylpentane; 6) 2,4-dimethylpentane; 7) 3,3-dimethylpentane; 8) 3-ethylpentane; and 9) 2,2,3-trimethylbutane.

The separator 20 separates out the multiple-branched alkanes 54. The mono-branched alkanes 56 and the linear pentanes, hexanes and heptanes 58 are preferably recycled back to the reactor for further processing. However, the linear and mono-branched alkanes can also be removed from the system for other uses.

In another embodiment, the mono-branched and linear alkanes are directed through a second separator with a second type of matrix or a second type of separation scheme such as condensation or distillation to further separate or isolate any desired components of the output feed mixtures. Alternatively, the second separator could be positioned before the separator of the invention to allow control over the specific separations.

Figure 6:
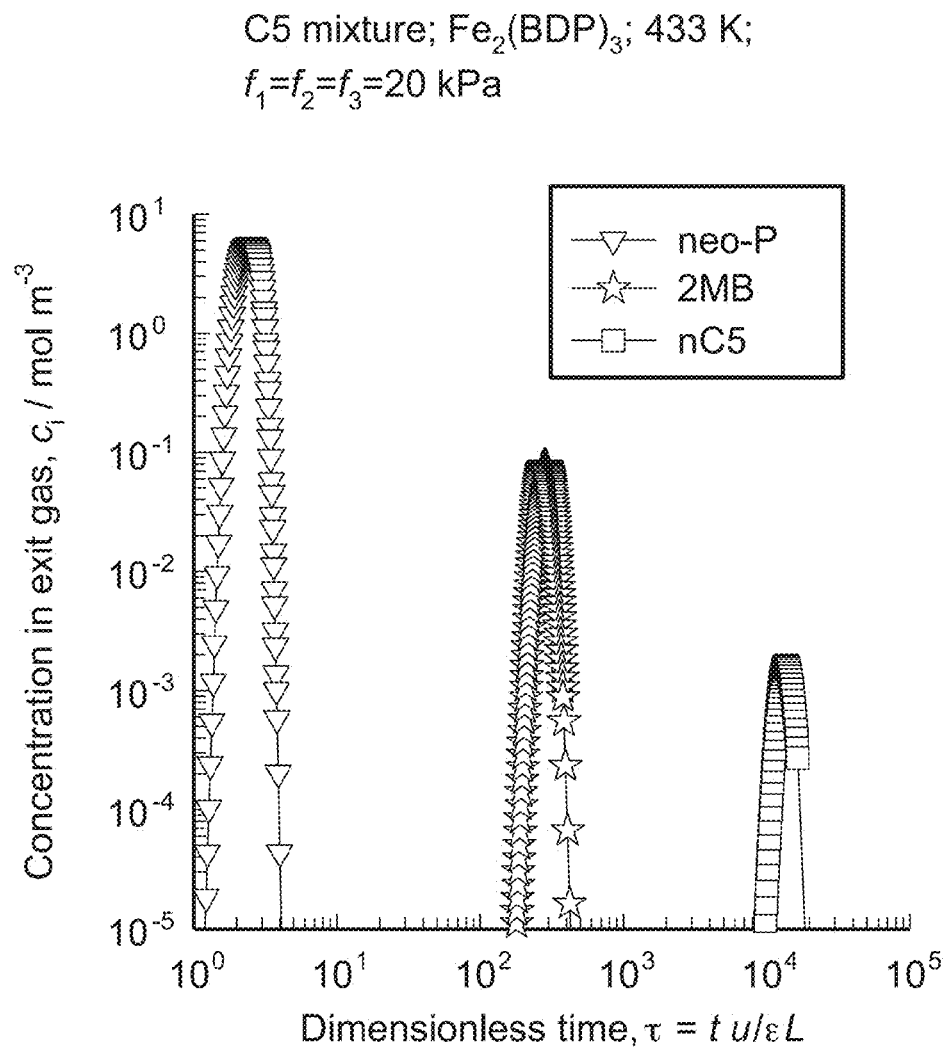
FIG. 6 is a pulse chromatograph of simulations for separation of a 3-component pentane mixture (nC5/2 MB/neoP) using $Fe_2(BDP)_3$ using pure component isotherm fits of CBMC simulations of component isotherms and assuming no diffusional influences.
Figure 6:
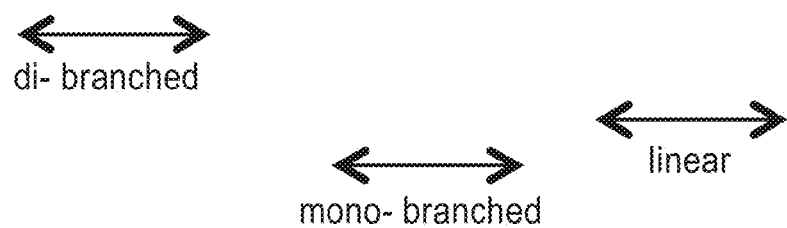

The systems shown schematically in FIG. 4, FIG. 5 and FIG. 6 may also include one or more valves in the separator outflow line that can be actuated to segregate the material emerging from the separator 20 to transfer lines to the isomerization reactor 12, the reactor input feed 14 or to a collector.

In other embodiments, the transfer lines from the separator 20 to the isomerization reactor 12 or the reactor input feed 14 include a storage container with valves that can store the separated and collected linear alkanes or mono-branched alkanes. Temporary storage in storage containers of separated alkanes permits a consistent flow of recycled alkanes without interruption when the source of alkanes from the separator does not have a consistent flow.

The systems shown schematically in FIG. 4, FIG. 5 and FIG. 6 may also include a controller such as a computer control system that has programming that monitors and controls the valve actuation timing as well as the pressure, temperature, volume and composition of the feed mixtures to the isomerization reactor 12, the separator 20 and the stored recycled alkanes. The manner in which the stored alkanes are introduced back to the isomerization reactor 12 or feed 14 can also be controlled with the controller so that the timing, the feed compositions, the isomerization reaction conditions and the separation conditions in the system can be optimized. The system controller can also control compressors, heating and cooling elements and associated sensors in addition to the timing and sequence of valve actuation in the feed lines and storage containers.

The invention may be better understood with reference to the accompanying examples, which are intended for purposes of illustration only and should not be construed as in any sense limiting the scope of the present invention as defined in the claims appended hereto.

Example 1

In order to demonstrate the functionality of the invention, the $Fe_2(BDP)_3$ material was synthesized and evaluated. A 100 ml Schlenk flask was charged with 6.04 g (17.1 mmol) of $Fe(acac)_3$ and 1.20 g (5.71 mmol) of benzenedipyrazolate ($H_2BDP$) and a magnetic stir bar. Then, 80 mL of dry, degassed N,N-dimethylformamide (DMF) was added to the Schlenk flask via cannula transfer. The reaction was refluxed under nitrogen for 18 hours. The black microcrystalline precipitate was collected on a Buchner funnel. This material was heated in dimethyl sulfoxide (DMSO) at 100° C. for 8 hours, and the DMSO was subsequently decanted.

The material was then washed 5 more times with heated DMSO and similarly washed six more times with DMF heated to 100° C. and then six more times with methylene chloride heated to 70° C. This washing procedure removed unreacted ligands, metal sources, polymerization products of DMF and solvents from previous washes.

The material was then heated under a 10 mTorr vacuum to 180° C. for 24 hours to remove guest solvent molecules. The resulting material had an FT-IR: (solid, ATR): $v_{C=C}$ 1576, $v_{C=N}$ 1384, 1342 cm$^{-1}$. An aliquot of the activated sample was then soaked in DMSO, filtered, dried in air and then examined by TGA and CHN analysis. The 16% weight-loss that was observed at 150° C. was consistent with a formulation of $Fe_2(BDP)_3 \cdot 1.75$ DMSO which was in agreement with CHN analysis. Anal. Calcd. for $Fe_8C_{158}H_{138}N_{48}S_7O_7$: C, 54.23; H, 4.18; N, 19.21. Found: C, 54.73; H, 3.82; N, 18.73.

Example 2

Pure-component equilibrium adsorption isotherms for the five different hexane isomers were measured for $Fe_2(BDP)_3$ at temperatures of 130° C., 160° C., and 200° C. as shown in FIG. 2. The measurements were taken within the temperature range of 100° C. to 200° C. that is the relevant range for the industrial separation of alkane gases. In contrast to conventional absorbers like zeolite 5A, which operates as a sieve for separating n-hexane, the dimensions of the channels in the evacuated structure of $Fe_2(BDP)_3$ are large enough to accommodate all five hexane isomers. Consequently, separation is dependent on the structure and adsorptive properties of the individual isomers.

For all gas adsorption measurements, 200-225 mg of $Fe_2(BDP)_3 \cdot 1.75$ DMSO was transferred to a pre-weighed glass sample tube under an atmosphere of nitrogen and capped. Samples were then transferred to Micromeritics ASAP 2020 gas adsorption analyzer and heated at a rate of 1° C./minute from room temperature to a final temperature of 180° C. Samples were considered activated when the outgas rate at 150° C. was less than 2 μbar/minute, which occurred approximately 48 hours after the start of evacuation. Evacuated tubes containing degassed samples were then transferred to a balance and weighed to determine the mass of the sample which typically ranged between 150-175 mg. The tube was transferred to the analysis port of the instrument where the outgas rate was again determined to be less than 2 μbar/minute at 180° C. Gas with 99.999% purity was used for nitrogen adsorption. All non-cryogenic measurements were performed using a sand bath connected to an automated temperature controller. Liquid hexane isomers were obtained from Sigma Aldrich and were added to the ASAP 2020 vapor adsorption apparatus. The liquids were frozen. The pressure was monitored until it reached a low of 0.001 mbar, and then the headspace was evacuated for 5 minutes. The solid was melted, and the freeze-pump thaw procedure was repeated two more times. The liquid was then distilled into a new sample tube three times, each time only collecting approximately 50% of the original volume.

At 130° C., the isotherm data was shown to rise with varying degrees of steepness until reaching saturation. The decreasing degrees of steepness in the isotherms for linear vs. mono-branched vs. di-branched isomers indicated a corresponding decrease in the adsorption strength. At 200° C., the isotherms rise considerably less sharply and do not reach saturation. At 160° C., n-hexane and the mono-branched isomers exhibit the behavior expected of an interpolation between the 130° C. and 200° C. isotherms: saturation capacity is reached or nearly reached, but at pressures higher than those required at 130° C. At approximately 100 mbar and 200° C., $Fe_2(BDP)_3$ adsorbs 60% more n-hexane by volume and 100% more by weight than zeolite 5A. This enhancement, together with the adsorption selectivity of the material, demonstrates that $Fe_2(BDP)_3$ is a much more efficient adsorbent than zeolite 5A for the n-hexane separation presently carried out in industry.

At 160° C., the two di-branched hexane isomers displayed a stepwise adsorption, with an inflection point near 100 mbar. The stepwise uptake of alkanes had been observed previously with cyclohexane and n-hexane adsorption, and can be explained with entropic arguments, as supported by calorimetric data. Here, the inflection point occurs near 0.5 moles of guest per mole of $Fe_2(BDP)_3$. It appears that rearrangement occurs at this loading based upon packing around the structural ridge that is created along the triangular channel by two adjacent $Fe_2(BDP)_3$ subunits. This was supported by simulations.

However, the behavior was not evident at 200° C., because a loading of 0.5 moles is not attained under the measured conditions. The step is not as prominent at 130° C. for two reasons: 1) the entropic component of the Gibbs free energy is smaller at lower temperatures and 2) the steepness of the isotherm obscures the feature.

Neutron diffraction data demonstrated the lack of a preferred arrangement of n-hexane molecules within the pores of $Fe_2(BDP)_3$ and confirmed the ordered adsorption of di-branched isomers. Diffraction patterns were collected at 10 K on microcrystalline powders loaded with 0.5 and 1.0 molar equivalents of perdeuterated n-hexane. Attempts to refine the position of the n-hexane molecules in both samples were thoroughly exhausted using several different refinement approaches, suggesting that there is unlikely any correlation between the positions of guests adsorbed in each pore.

The enthalpy of adsorption of the five hexane isomers in $Fe_2(BDP)_3$ was shown to be dependent on the degree of branching of the gas molecule. Isosteric heats of adsorption were calculated by differentiation of the temperature-independent, combined dual-site Langmuir-Freundlich fits to the isotherm data obtained at 130° C., 160° C., and 200° C. For hexane isomer separations, the experimentally determined isotherm fits and parameter values from Table 2 were used. In order to report enthalpy values obtained without extrapolation, the results were only plotted up to the highest loading attained at the highest temperature. The linear n-hexane isomer had the strongest interaction with the framework, because a greater fraction of its surface could interact with the triangular channel pore surface than observed with the other isomers.

Comparing methylpentane isomers, the zero-coverage isosteric heat was initially very similar, but as more guests entered the pores, the strength of interaction of the two isomers diverged. Here, the higher flexibility of the 2-methyl pentane chain apparently allows a stronger adsorbate-adsorbent interaction to be maintained at higher loadings. The bulkier dimethylbutane isomers are not flexible enough to maximize van der Waals interactions with the pore surfaces and have the lowest enthalpies at all loadings. This trend in selectivity has occasionally been observed at very low loadings in zeolites as a result of different isomers residing in different parts of a heterogeneous pore structure, but at more substantial loadings it disappears. In contrast, for $Fe_2(BDP)_3$, the isomers are all interacting with the same, relatively-homogeneous surface differently.

Taken together, the trends in the enthalpy and entropy of adsorption for the five hexane isomers demonstrated a free energy hierarchy of linear>mono-branched>di-branched isomer adsorption. The linear isomers bind more strongly and additionally do not require substantial reorganization at loadings above 0.5 molecules per unit cell.

Example 3

In order to investigate the fundamental reasons for the hierarchy of adsorption strengths observed in the experiments, Configurational-Bias Monte Carlo (CBMC) simulations of adsorption were conducted. The CBMC simulations illustrate and support the mechanism of alkane isomer fractionation in $Fe_2(BDP)_3$. The CMBC simulations demonstrated the unique efficacy of $Fe_2(BDP)_3$ in separating hexane isomers according to the degree of branching.

The CBMC simulation methodology first determined the pure component isotherms for nC5, 2 MB, neoP, nC6, 2MP, 3MP, 22DMB, 23DMB, nC7, 2MH, 3MH, 22DMP, and 23DMP in $Fe_2(BDP)_3$ at 433 K for a wide range of pressures ranging to 0.1 Pa to 10 MPa. These pure component isotherms were fitted with the dual-site Langmuir-Freundlich model to yield the parameters and the fits were found to be excellent.

For the hexane isomers, the hierarchy of loadings nC6>2MP 3MP>22DMB≈23DMB was precisely the same as that obtained in the experiments described in Example 2. CMBC simulations also indicated that $Fe_2(BDP)_3$ is similarly suitable for separating pentane and heptane isomers according to the degree of branching. For pentane isomers, the results indicate the hierarchy of adsorption strengths as n-pentane (nC5)>2-methylbutane (2 MB)>neopentane (neoP). For the heptanes, adsorption strengths follow the order n-heptane (nC7)>2-methylhexane (2MH)≈3-methylhexane (3MH)>2,2-dimethylpentane (22DMP)≈2,3-dimethylpentane (23DMP).

These hierarchies may be best rationalized by examining the location and conformation of each isomer within the triangular channels of the framework. Snapshots were taken from arbitrary channel segments showing the location and conformations of pentane, hexane and heptane isomers adsorbed within the triangular channels of $Fe_2(BDP)_3$. The backbone of nC5 was shown to align along the gutters, as was the case with nC6. The compact neo-P molecule exerts the least amount of van der Waals interactions with the pore walls, and consequently has the lowest adsorption strength.

Generally, the hexane backbones align along the vertices of the triangular channels, which provide the maximum surface area for dispersion interactions. The regularity of the 2,3-dimethylbutane and 2,2-dimethylbutane positions is consistent with the idea that these molecules have a preferred arrangement, one that requires energy input to overcome and that van der Waals overlap decreases with the degree of branching. From the observed conformations, it was evident that the number of carbon atoms that can effectively interact with the pore wall decreases with the degree of branching. The dimethylbutane isomers are more compact and have the weakest van der Waals interactions with the framework surface.

The CMBC calculations also suggested that the size of the channels in $Fe_2(BDP)_3$ are nearly optimal for hexane isomer separations. Narrower triangular channels cannot accommodate all five isomers, while wider channels do not maximize the differences in van der Waals contacts. Furthermore, pulse chromatography simulations revealed the extraordinary ability of $Fe_2(BDP)_3$ to separate the di-branched alkanes with high RON values from a mixture of pentane, hexane, and heptane isomers.

Example 4

In order to further demonstrate the functionality of the invention, the hexane isomer separation capability of $Fe_2(BDP)_3$ was evaluated with breakthrough experiments, in which an equimolar mixture of all five isomers in $N_2$ was passed over a bed of the material heated at 160° C. The bed was a column of 0.491 g of $Fe_2(BDP)_3$ that was packed into a glass u-tube, with an internal diameter of 0.9525 cm. The height of the sample was 11.5 cm. Dry $N_2$ at a rate of 2.5 mL/min was bubbled through a mixture of hexane isomers according to the following volumes: 2.67 mL of 2,2-dimethylbutane, 3.50 mL of 2,3-dimethylbutane, 3.79 mL of 2-methylpentane, 4.22 mL of 3-methylpentane, and 5.82 mL of n-hexane. These volumes were determined through trial and error. The experiment was run without any sample and the vapor phase ratios were optimized to an equimolar final product. The effluent was passed through a VICI Valco 6-way sampling valve. Every minute, a 0.25 mL aliquot of gas was delivered to a Perkin Elmer Glarus 500 gas chromatograph fitted with a Supelco Equity-1 capillary GC column, 15 m long, with a 0.1 mm outside diameter and 0.10 μm poly(dimethyl sulfoxane) coating, submerged in an ice water bath. All five peaks were separated and easily integrated in the resulting GC trace.

It was observed that pure 2,2-dimethylbutane eluted from the bed first, followed by 2,3-dimethylbutane. These di-branched isomers are the most desirable, owing to their high RON values. Mono-branched 2-methylpentane eluted thereafter, immediately followed by 3-methylpentane, and then, much later, linear n-hexane.

During the beginning of the breakthrough experiment, the RON of the product mixture leaving the column was seen to rise to greater than 90, significantly higher than the value of 83 that is typical for industrially-refined hexane blends.

The shape of the breakthrough curve for each isomer is informative with regard to the separation. The steepness of the dimethylbutane breakthrough events suggested that the separations for these isomers result from essentially equilibrium processes and are not diffusion controlled.

It was also observed that the enthalpy of adsorption for the two dimethylbutane isomers is essentially identical up to a loading of 0.6 mmol/g. If diffusion is not the primary cause of the separation, and the material is saturated at the breakthrough event, the strength of adsorption of these isomers presumably diverges at higher loadings, with 2,3-dimethylbutane adsorbing more strongly. The methylpentanes and n-hexane displayed more gradual breakthrough events, suggesting that diffusion is a contributory factor in their elution dynamics.

In the initial phase of the adsorption cycle, the exit gas stream is richer in the di-branched isomers. As a consequence the RON of the product gas stream has the highest RON values near the start of the cycle, approaching 100. In all of the calculations, the RON of the hydrocarbon mixture was calculated from the pure component RON values in Table 2 averaged over the exit gas composition and no non-linear mixing rules were applied.

Predictably, the RON of the product gas dropped significantly with the commencement of the breakthroughs of the mono-branched isomers, 2MP and 3MP. For the chosen set of operating conditions, a material balance on the adsorber yields information on the amount of 92 RON products that can be recovered. It should be noted that this value of 92 was obtained by averaging the overall isomers in the gas phase for the appropriate time interval.

The 92 RON productivity, calculated on the basis of the amount of crystalline adsorbent $Fe_2(BDP)_3$ in the packed adsorber, was 0.67 mol $kg^{-1} \equiv$ 0.77 mol $L^{-1}$. The volumetric productivity is obtained by multiplying the gravimetric productivity by the framework density $\rho$=1.145 kg $L^{-1}$.

The assumption of thermodynamic equilibrium tends to produce sharp breakthroughs while the experimental breakthroughs were shown to be more "diffuse," suggesting that intra-crystalline diffusion limitations are occurring. Therefore, in order to obtain a more realistic estimate of 92 RON productivity, breakthrough calculations that included diffusional influences were performed. For hexane isomers in $Fe_2(BDP)_3$, the values of the Fick diffusivities $D_i$ were taken to be those found in ZIF-77 at 433 K since the channels of ZIF-77 are 4.5 Å in size, similar to that of $Fe_2(BDP)_3$, and the diffusivities in these two materials were expected to be similar in magnitude.

Accordingly, the organic-metal $Fe_2(BDP)_3$ is suitable for use with separations of many different alkanes and other branched hydrocarbons based on branching rather than the number of carbons in the molecules.

Example 5

The ability of $Fe_2(BDP)_3$ to fractionate a mixture of 5-component hexane isomer mixtures was also confirmed by breakthrough calculations in which use CBMC simulations of pure component isotherms in place of the experimentally determined ones. In view of this agreement, CBMC simulations and the experimental data in $Fe_2(BDP)_3$, the molecular simulations could be confidently used to further investigate the feasibility of separating other alkane isomer mixtures.

FIG. 6 shows the pulse chromatographic simulation results for separation of pentane isomers. This separation of pentane isomers is of importance to the petrochemical industry because 2 MB is used as a solvent and as feedstock for production of isoprene by oxidative dehydrogenation. The ability of $Fe_2(BDP)_3$ to separate the mixture into individual fractions offers the possibility of supplanting conventionally used energy-intensive distillation (called de-isopentanizers) with more efficient adsorptive separations.

Figure 7:
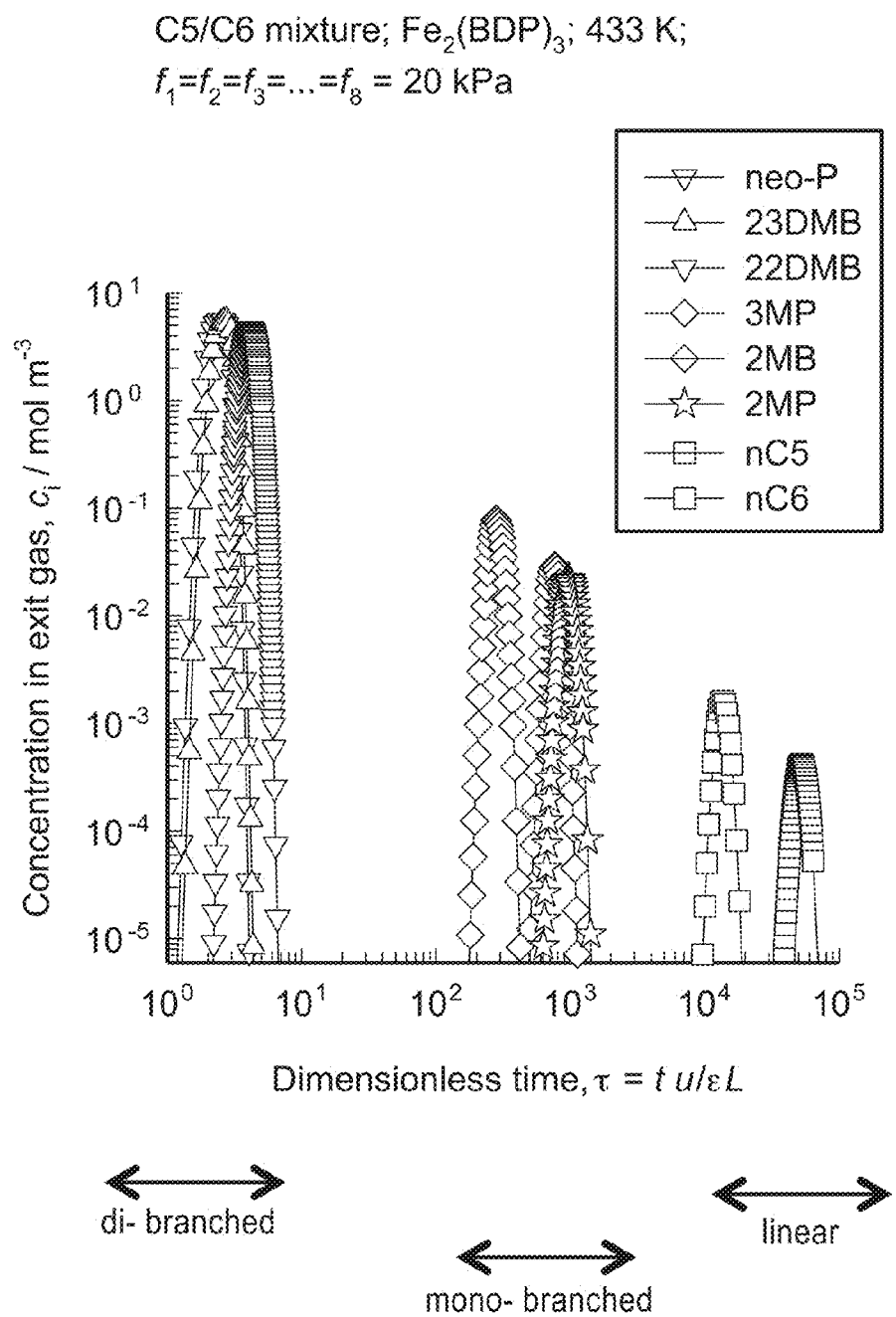
FIG. 7 is a pulse chromatograph of simulations for separation of an 8-component pentane/hexane mixture (nC5/2 MB/neoP/nC6/2MP/3MP/-22DMB/23DMB) using $Fe_2(BDP)_3$ using pure component isotherm fits of CBMC simulations of component isotherms and assuming no diffusional influences.

In industrial practice, the feed to the isomerization reactor also contains the C5 and C7 alkane isomers. So the potential of $Fe_2(BDP)_3$ for separating C5/C6 and C5/C6/C7 mixtures was also investigated. FIG. 7 shows the pulse chromatographic simulations for separation of 8-component pentanes/hexanes mixture: nC5/2 MB/neoP/nC6/2MP/–3MP/22DMB/23DMB using $Fe_2(BDP)_3$. The separation into three fractions based on the degree of branching, rather than on carbon numbers, was evident. The implications of this fractionation ability is that it is possible to utilize $Fe_2(BDP)_3$ in the separation step of a C5/C6 alkane isomerization process.

Figure 8:
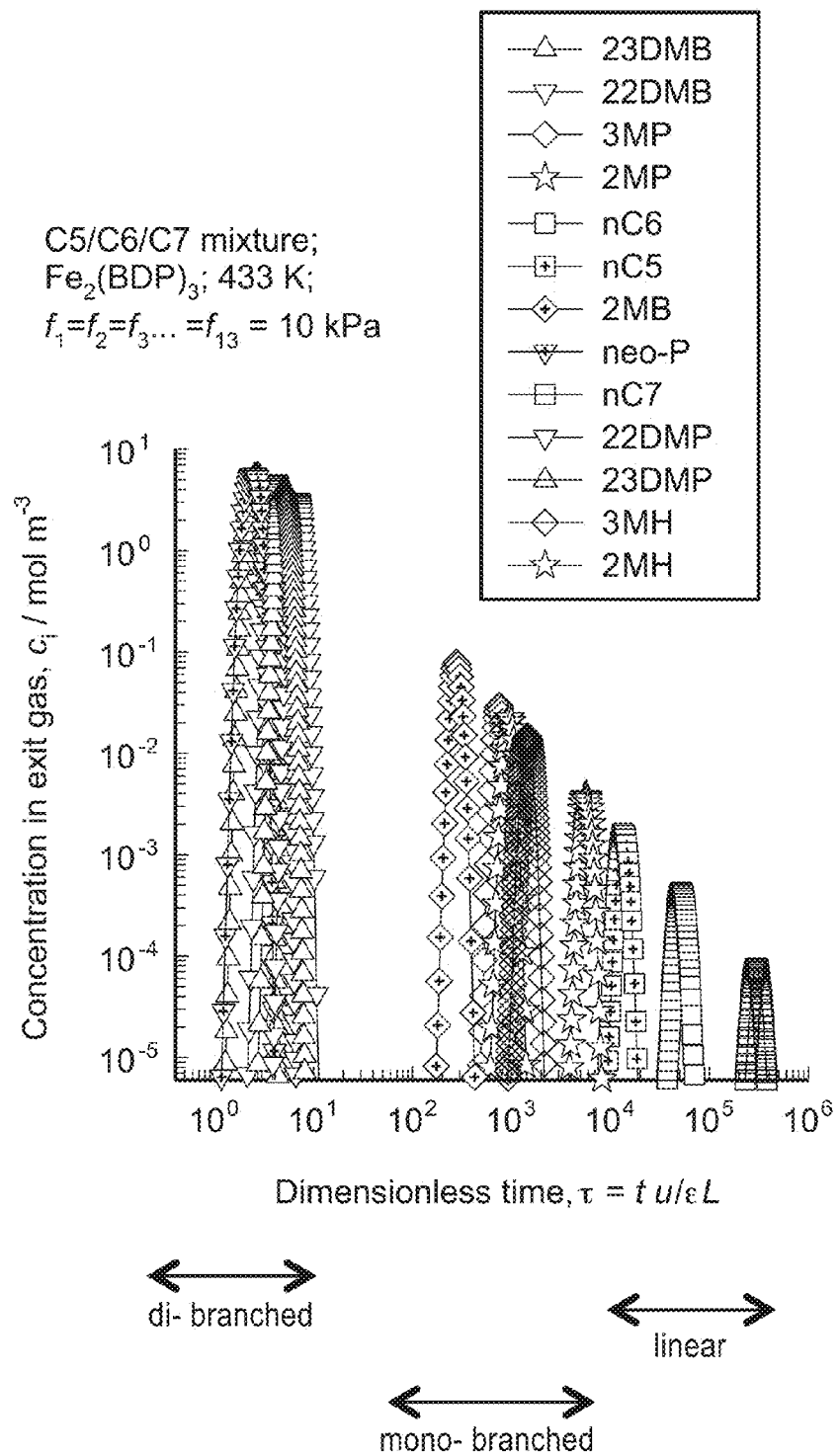
FIG. 8 is a pulse chromatograph of simulations for separation of a 13-component pentane/hexane/heptane mixture of (nC5/2 MB/neoP/nC6/-2MP/3MP/22DMB/23DMB/nC7/2MH/3MH/22DMP/23DMP) using $Fe_2(BDP)_3$ using pure component isotherm fits of CBMC simulations of component isotherms and assuming no diffusional influences.

Likewise, this fractionation ability can be illustrated with the use of $Fe_2(BDP)_3$ in the separation step of a C5/C6/C7 alkane isomerization process scheme. FIG. 8 presents the pulse chromatographic simulation results for separation of the 13-component (pentanes/hexanes/heptanes) mixture: nC5/2 MB/neoP/nC6/2MP/3MP/22DMB/23DMB/nC7/2MH/3MH/22DMP/23D MP. The separation into three fractions based on the degree of branching, rather than on carbon numbers, was also observed.

Simulations of breakthrough characteristics of a fixed bed adsorber packed with $Fe_2(BDP)_3$ operating at a total pressure of 100 kPa and 433 K were performed that assumed thermodynamic equilibrium and no diffusional limitations. As expected, the sequence of breakthroughs was the same in the simulations as observed in the breakthrough experiments.

The values of D, used in the breakthrough simulations were: nC6: $5 \times 10^{-10}$ $m^2$ $s^{-1}$; 2MP: $1 \times 10^{-10}$ $m^2$ $s^{-1}$; 3MP: $1 \times 10^{-10}$ $m^2$ $s^{-1}$; 22DMB: $5 \times 10^{-11}$ $m^2$ $s^{-1}$ and 23DMB: $5 \times 10^{-11}$ $m^2$ $s^{-1}$. The value of the crystallite radius, $r_c$, used in the breakthrough simulation was 500 μm, that is typical of PSA operations. Consequently, $D_{nC6}/r_c^2$=0.002 $s^{-1}$; $D_{nC6}/D_{2MP}$=5; $D_{nC6}/D_{3MP}$=5; $D_{nC6}/D_{22DMB}$=10; $D_{nC6}/D_{23DMB}$=10.

The breakthrough simulations that included diffusion influences demonstrated breakthrough fronts that were less sharp, and more in line with those observed experimentally. More diffuse breakthroughs have the effect of lowering the RON productivity in relation to the equilibrium simulations. The 92 RON productivity, obtained from a material balance, was 0.47 mol $kg^{-1} \equiv$ 0.54 mol $L^{-1}$.

It can be seen that the $Fe_2(BDP)_3$ material is an effective alternative to existing schemes for producing high octane gasoline from the conventional reactor output. However, the ability of $Fe_2(BDP)_3$ to "fractionate" the mixture of hexanes into three separate fractions, consisting of linear nC6, monobranched 2MP and 3MP, and di-branched 22DMB and 23DMB is more than what is demanded by the conventional gasoline processing systems that requires only separation between mono- and di-branched isomers.

The capability of $Fe_2(BDP)_3$ to separate isomers according to branching permits the material to be used in a variety of new separation schemes such as those shown in FIG. 3 through FIG. 5. With staged recycling, the possibility exists of improving the conversion of the reaction step with a potential increase in conversion and yields for a given reactor volume. For example, the linear nC6 can be mixed with the incoming feed mixture to the isomerization reactor. The mono-branched isomers 2MP and 3MP can also be recycled to an intermediate location in the reactor.

Finally, the validity of IAST estimations of adsorption of alkane isomer mixtures in $Fe_2(BDP)_3$ was established to substantiate the breakthrough calculations. For this purpose CBMC simulations were carried out for adsorption of four different equimolar mixtures in $Fe_2(BDP)_3$ at 433 K: 3-component pentanes: (nC5/2 MB/neoP), 5-component hexanes (nC6/2MP/3MP/22DMB/23DMB) 8-component pentanes/hexanes: (nC5/2 MB/neoP/nC6/2MP/3MP/22DMB/23DMB), and 13-component pentanes/hexanes/heptanes (nC5/2 MB/neoP/nC6/2MP/3MP/22DMB/–23DMB/nC7/2MH/3MH/22DMP/23DMP).

For all mixtures there was an excellent agreement between the CBMC simulated component loadings and the IAST calculations. Having established the accuracy of IAST calculations, it was possible to proceed with the breakthrough calculations detailed in Example 4.

Example 6

To demonstrate the superior performance of and functionality of the invention, the separation performance of $Fe_2(BDP)_3$ was compared with that of other conventional microporous adsorbents for hexane isomer separations. Adsorbents for comparison were selected based on suggested or existing uses with the separation of hexane isomers. Zeolites (MFI, CFI, ATS, BETA, MWW), metal-organic frameworks (UiO-66, Zn(bdc)dabco, ZnHBDC, IM-2), and zeolite imidazolate frameworks (ZIFs) ZIF-8 and ZIF-76 were considered for comparison.

These materials cover a wide range of pore sizes, pore topologies and connectivities. For the purposes of making comparisons with the performance of $Fe_2(BDP)_3$, data obtained from CBMC simulations of pure component and mixture isotherms from the recent published literature was used because pure component isotherms for each of the five isomers was not available for these materials. For the evaluation of different adsorbents for a given separation task, the two commonly used metrics are adsorption selectivity and uptake capacity.

For a binary mixture, the adsorption selectivity was defined as follows:

$$S_{ads} = \frac{q_1/q_2}{f_1/f_2}.$$

For comparative evaluation of the different adsorbents the extension of this definition for separation of 5-component mixture of nC6 (=component 1), 2MP (=component 2), 3MP (=component 3), 22DMB (=component 4), and 23DMB (=component 5), each with partial fugacities, $f_i$, is not straightforward because the hierarchy of adsorption strengths is not the same for all materials.

For some materials, such as MFI, and $Fe_2(BDP)_3$ there is a "normal" hierarchy wherein, the linear nC6 has the highest adsorption strength and the di-branched isomers the weakest adsorption strength. For other materials such as UiO-66, MWW, and CFI there is a "reverse" hierarchy wherein the di-branched isomers have the highest adsorption strength, and the linear nC6 isomer has the weakest adsorption strength.

Comparisons of various materials with $Fe_2(BDP)_3$ were made by determining the 92 RON productivities in fixed bed adsorbers using breakthrough simulations. For each material, we choose identical set of conditions for comparison: total pressure, $p_t$=100 kPa, equimolar feed of 5-component hexane isomer mixture ($p_1$=$p_2$=$p_3$=$p_4$=$p_5$=20 kPa); temperature, T=433 K. The adsorbents chosen for comparison are those for which there is experimental data confirming the separation potential. The comparisons also took into account whether the material had a "normal" or "reverse" or "mixed" hierarchy. The results of the comparisons are found in Table 3. Based on the comparisons, $Fe_2(BDP)_3$ emerges as the adsorbent with the best 92 RON productivity.

Overall comparisons of $Fe_2(BDP)_3$ with other adsorbents of relevance in industrial operations, were obtained by comparing the number of moles of 92 RON product that can be obtained per liter of adsorbent in a packed bed adsorber, taking account of diffusional limitations. These comparisons showed that for $Fe_2(BDP)_3$ the 92 RON productivity is 0.54 mol/L, whereas the values obtained for other adsorbents were consistently lower.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. A method of separating alkane isomer mixtures, comprising: providing a source of alkane isomers; streaming the alkane isomers through a separator bed of $Fe_2(BDP)_3$ to separate the alkane isomers according to the degree of branching; collecting branched isomers separated from the stream of alkane isomers; and collecting mono-branched and linear alkanes separated from the stream of alkane isomers.

2. A method as recited in any previous embodiment, further comprising: producing the source of alkane isomers with an isomerization reactor.

3. A method as recited in any previous embodiment, further comprising: recycling the collected linear alkanes to the isomerization reactor for isomerization.

4. A method as recited in any previous embodiment, further comprising: recycling the collected mono-branched alkanes to the isomerization reactor for isomerization.

5. A method as recited in any previous embodiment, further comprising: controlling linear alkane concentration introduced to the isomerization reactor with collected linear alkanes.

6. A method as recited in any previous embodiment, further comprising: controlling mono-branched alkane concentration introduced to the isomerization reactor with collected mono-branched alkanes.

7. A method as recited in any previous embodiment, further comprising: introducing recycled mono-branched alkanes and recycled linear alkanes sequentially into the isomerization reactor.

8. A method as recited in any previous embodiment, further comprising: controlling the temperature and pressure of the alkane isomers streaming through the separator bed.

9. A method as recited in any previous embodiment, wherein the temperature and pressure of the alkane isomers streaming through the separator bed is the same temperature and pressure as produced by the isomerization reactor.

10. A method as recited in any previous embodiment, wherein the alkane isomers comprise hexane isomers and the collected branched isomers comprise 2,2-dimethylpentane (22DMP) and 2,3-dimethylpentane (23DMP).

11. A method as recited in any previous embodiment, wherein said alkane isomers comprise C5 and C6 isomers and the collected branched isomers comprise 2,2-dimethylpropane (neoP), 2,2-dimethylpentane (22DMP) and 2,3-dimethylpentane (23DMP).

12. A method as recited in any previous embodiment, wherein the alkane isomers comprise C5, C6 and C7 isomers and the collected branched isomers comprise 2,2-dimethylpentane (22DMP) and 2,3-dimethylpentane (23DMP); 2,4-dimethylpentane; 3,3-dimethylpentane; 3-ethylpentane; and 2,2,3-trimethylbutane.

13. A system for forming and separating branched alkane isomers, comprising: a feedstock of one or more alkanes; an isomerization reactor with an input feed coupled to the feedstock of alkanes and an output feed of reactor products; and a separator with a housing, a separator bed of $Fe_2(BDP)_3$, an intake duct coupled to the output feed of the isomerization reactor and at least one separation product outflow line coupled to the isomerization reactor and to a collector; wherein linear and mono-branched alkanes from the separation product line are returned to the isomerization reactor for further isomerization and multiple branched alkanes are collected.

14. A system as recited in any previous embodiment, further comprising: a storage container fluidly connected to the separator product outflow line and the isomerization reactor input feed; wherein linear alkanes are stored for controlled introduction into the isomerization reactor input feed.

15. A system as recited in any previous embodiment, further comprising: a storage container fluidly connected to the separator product outflow line and the isomerization reactor; wherein mono-branched alkanes are stored for controlled introduction into the isomerization reactor.

16. A system as recited in any previous embodiment, further comprising: a segregator valve fluidly coupled to the separation product outflow line, input feed, isomerization reactor and collector; wherein products from the separator outflow line are segregated to the isomerization reactor input feed, the isomerization reactor or to the collector.

17. A system as recited in any previous embodiment, further comprising: a system controller configured to control the segregator valve and flow of products to the isomerization reactor input feed, the isomerization reactor and to the collector.

18. A system as recited in any previous embodiment, wherein the system controller is configured to control the composition of the feedstock of the input feed and mono-branched alkanes in the isomerization reactor.

19. A porous metal organic framework comprising $Fe_2(bdp)_3$ ($BDP^{2-}$=1,4-benzenedipyrazolate).

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Research Octane Numbers (RON) of C5, C6, and C7 alkanes

| Alkane | | Research Octane Number |
|---|---|---|
| Symbol | Chemical Name | (RON) |
| nC4 | n-butane | 94 |
| iC4 | iso-butane = 2-methyl propane | 102 |
| nC5 | n-pentane | 61.7 |
| 2MB | 2-methyl butane | 93.5 |
| neoP | 2,2 dimethyl propane | 98 |
| nC6 | n-hexane | 30 |
| 2MP | 2-methyl pentane | 74.5 |
| 3MP | 3-methyl pentane | 75.5 |
| 22DMB | 2,2 dimethyl butane | 94 |
| 23DMB | 2,3 dimethyl butane | 105 |
| nC7 | n-heptane | 0 |
| 2MH | 2-methyl hexane | 42.4 |
| 3MH | 3-methyl hexane | 52 |
| 22DMP | 2,2 dimethyl pentane | 92.8 |
| 23DMP | 2,3 dimethyl pentane | 91.1 |

TABLE 2

Dual-Langmuir-Freundlich parameter fits for $Fe_2(BDP)_3$

| | Site A | | | | Site B | | | |
|---|---|---|---|---|---|---|---|---|
| | $q_{A,sat}$ mol kg$^{-1}$ | $b_{A0}$ Pa$^{-v_i}$ | $E_A$ kJ mol$^{-1}$ | $v_A$ dimensionless | $q_{B,sat}$ mol kg$^{-1}$ | $b_{B0}$ Pa$^{-v_i}$ | $E_B$ kJ mol$^{-1}$ | $v_B$ dimensionless |
| nC6 | 0.28 | $2.74 \times 10^{-26}$ | 111 | 3 | 1.17 | $8.86 \times 10^{-13}$ | 73 | 1.02 |
| 2MP | 0.78 | $2.13 \times 10^{-13}$ | 76 | 1.1 | 0.63 | $5.61 \times 10^{-17}$ | 89 | 1.36 |
| 3MP | 0.36 | $4.62 \times 10^{-13}$ | 76 | 1.1 | 1.07 | $1.34 \times 10^{-16}$ | 89 | 1.36 |
| 22DMB | 0.53 | $1.33 \times 10^{-32}$ | 167 | 2.9 | 0.94 | $1.42 \times 10^{-12}$ | 67 | 1 |
| 23DMB | 0.61 | $9.74 \times 10^{-33}$ | 167 | 2.9 | 0.92 | $1.49 \times 10^{-12}$ | 67 | 1 |

TABLE 3

Summary Of 92 RON Productivities Of Selected Adsorbents

| Adsorbent | 92 RON Productivity Calculated with Diffusion Effects (mol/L) | Notable limitations |
|---|---|---|
| $Fe_2(BDP)_3$ | 0.54 | |
| MWW Zeolite | <0.52 | Severe diffusional limitations |
| MFI Zeolite | 0.51 | Can't separate C5/C6/C7 mixtures |
| Zn(bdc)(dabco) | 0.48 | Mixed hierarchy |
| ZIF-8 | 0.46 | ZIF-8 relies on differences in diffusivities of isomers, not on adsorption |
| Zeolite BETA | 0.36 | |
| UiO-66 | 0.36 | |
| MIL-140C | 0.25 | |
| ZnHBDC | 0.2 | |
| MIL-140D | 0.2 | |
| CFI Zeolite | 0.175 | |
| ATS Zeolite | 0.17 | |

What is claimed is:

1. A method of separating alkane isomer mixtures, the method comprising:
   (a) providing a source of alkane isomers;
   (b) streaming the alkane isomers through a separator bed of $Fe_2(BDP)_3$ to separate the alkane isomers according to the degree of branching;
   (c) collecting di-branched isomers separated from the stream of alkane isomers; and
   (d) collecting mono-branched and linear alkanes separated from the stream of alkane isomers.

2. A method as recited in claim 1, further comprising producing the source of alkane isomers with an isomerization reactor.

3. A method as recited in claim 2, further comprising recycling the collected linear alkanes to the isomerization reactor for isomerization.

4. A method as recited in claim 3, further comprising recycling the collected mono-branched alkanes to the isomerization reactor for isomerization.

5. A method as recited in claim 2, further comprising controlling linear alkane concentration introduced to the isomerization reactor with collected linear alkanes.

6. A method as recited in claim 2, further comprising controlling mono-branched alkane concentration introduced to the isomerization reactor with collected mono-branched alkanes.

7. A method as recited in claim 2, further comprising introducing recycled mono-branched alkanes and recycled linear alkanes sequentially into the isomerization reactor.

8. A method as recited 1, further comprising controlling the temperature and pressure of the alkane isomers streaming through the separator bed.

9. A method as recited in claim 8, wherein the temperature and pressure of the alkane isomers streaming through the separator bed is the same temperature and pressure as produced by the isomerization reactor.

10. A method as recited in claim 1, wherein said alkane isomers comprise hexane isomers and the collected branched isomers comprise 2,2-dimethylpentane (22DMP) and 2,3-dimethylpentane (23DMP).

11. A method as recited in claim 1, wherein said alkane isomers comprise C5 and C6 isomers and the collected branched isomers comprise 2,2-dimethylpropane (neoP), 2,2-dimethylpentane (22DMP) and 2,3-dimethylpentane (23DMP).

12. A method as recited in claim 1, wherein said alkane isomers comprise C5, C6 and C7 isomers and the collected branched isomers comprise 2,2-dimethylpentane (22DMP) and 2,3-dimethylpentane (23DMP); 2,4-dimethylpentane; 3,3-dimethylpentane; 3-ethylpentane; and 2,2,3-trimethylbutane.

13. A system for forming and separating branched alkane isomers, the system comprising:
   (a) a feedstock of one or more alkanes;
   (b) an isomerization reactor with an input feed coupled to said feedstock of alkanes and an output feed of reactor products; and
   (c) a separator with a housing, a separator bed of $Fe_2(BDP)_3$, an intake duct coupled to the output feed of the isomerization reactor and at least one separation product outflow line coupled to the isomerization reactor and to a collector;
   (d) wherein linear and mono-branched alkanes from the separation product line are returned to the isomerization reactor for further isomerization and multiple branched alkanes are collected.

14. A system as recited in claim 13, further comprising:
a storage container fluidly connected to the separator product outflow line and the isomerization reactor input feed;
wherein linear alkanes are stored for controlled introduction into the isomerization reactor input feed.

15. A system as recited in claim 13, further comprising:
a storage container fluidly connected to the separator product outflow line and the isomerization reactor;
wherein mono-branched alkanes are stored for controlled introduction into the isomerization reactor.

16. A system as recited claim 13, further comprising:
a segregator valve fluidly coupled to the separation product outflow line, input feed, isomerization reactor and collector;

wherein products from the separator outflow line are segregated to the isomerization reactor input feed, the isomerization reactor or to the collector.

17. A system as recited in claim 16, further comprising a system controller configured to control the segregator valve and flow of products to the isomerization reactor input feed, the isomerization reactor and to the collector.

18. A system as recited in claim 17, wherein said system controller is configured to control the composition of the feedstock of the input feed and mono-branched alkanes in the isomerization reactor.

19. A porous metal organic framework comprising $Fe_2(bdp)_3$ ($BDP^{2-}$=1,4-benzenedipyrazolate).

* * * * *